United States Patent [19]

White et al.

[11] 3,965,112
[45] June 22, 1976

[54] IMIDAZOLINE DERIVATIVES

[75] Inventors: Alan Chapman White, Windsor; Robin Michael Black, Porton, both of England

[73] Assignee: John Wyeth & Brother Limited, Taplow, England

[22] Filed: May 29, 1975

[21] Appl. No.: 582,043

Related U.S. Application Data

[63] Continuation-in-part of Ser. No. 472,759, May 23, 1974, Pat. No. 3,926,994, and a continuation-in-part of Ser. No. 309,580, Nov. 24, 1972, abandoned.

[52] U.S. Cl............................. 260/309.6; 424/273
[51] Int. Cl.[2]......................................... C07D 49/34
[58] Field of Search................................. 260/309.6

[56] References Cited
UNITED STATES PATENTS

| | | | |
|---|---|---|---|
| 2,899,441 | 8/1959 | Dornfeld | 260/309.6 |
| 3,483,203 | 12/1969 | Werner | 260/309.6 X |

FOREIGN PATENTS OR APPLICATIONS

| | | | |
|---|---|---|---|
| 1,259,005 | 1/1972 | United Kingdom | 260/309.6 |

*Primary Examiner*—Ethel G. Love

[57] ABSTRACT

The disclosure relates to derivatives of imidazoline of the general formula

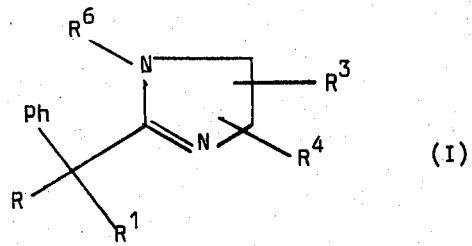

or pharmaceutically acceptable acid addition salts thereof wherein $R^3$ and $R^4$ which may be the same or different each represent hydrogen or lower alkyl, Ph represents phenyl, halophenyl, lower alkyl phenyl, di(-lower alkyl) phenyl or lower alkoxy phenyl, R is hydroxyl, lower alkoxy or halogen, $R^1$ is phenyl, halophenyl, lower alkyl phenyl, di(lower alkyl)phenyl, lower alkoxy phenyl or napthyl and $R^6$ is hydrogen or lower alkyl. The compounds have hypoglycemic activity.

4 Claims, No Drawings

IMIDAZOLINE DERIVATIVES

This application is a continuation-in-part of co-pending U.S. patent application Ser. No. 472759 filed May 23, 1974 entitled "Heterocylic Compounds", now U.S, Pat. 3,926,994 which in turn is a continuation-in-part of U.S. patent application Ser. No. 309,580 filed Nov. 24, 1972 entitled "Heterocyclic compounds", now abandoned.

This invention relates to derivatives of imidazoline, to processes for preparing these compounds and to pharmaceutical preparations containing them.

The compounds of the present invention are those of general formula

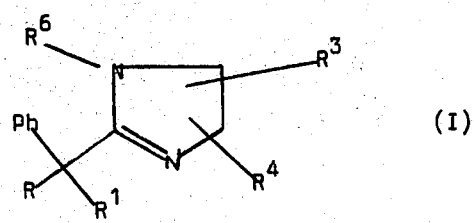

and their pharmaceutically acceptable acid addition salts, wherein $R^3$ and $R^4$ which may be the same or different each represent hydrogen or lower alkyl, Ph represents phenyl, halophenyl, lower alkyl phenyl, di (lower alkyl)phenyl or lower alkoxy phenyl, R is hydroxy lower alkoxy or halogen, $R^1$ is phenyl, halophenyl, lower alkyl phenyl, di(lower alkyl)phenyl, lower alkoxy phenyl or naphthyl and $R^6$ is hydrogen or lower alkyl.

Since the compounds of the invention may possess one or more asymmetric carbon atoms, optical enantiomorphs are possible and the compound of the invention may be in the form of the pure enantiomorphs or mixtures of such enantiomorphs, such as racemates.

The term "lower" as used herein means that the radical referred to contains up to 6, preferably up to 4 carbon atoms. It is to be understood that $R^3$ and $R^4$ may be on the same or different carbon atoms, but preferably they are both on the same carbon atom.

In the compounds of formula (I) examples of R groups are hydroxyl; lower alkoxy groups (e.g. methoxy, ethoxy, n-propoxy, n-butoxy), and halo groups such as chloro. Preferably R is hydroxy.

Examples of the group $R^1$ are phenyl, halophenyl (for example, fluorophenyl, chlorophenyl of bromophenyl), lower alkyl phenyl or di (lower alkyl)phenyl (where the lower alkyl substituents may be, for example, methyl, ethyl, propyl or butyl), lower alkoxy phenyl (for example methoxyphenyl, ethoxyphenyl, propoxyphenyl or butoxyphenyl) and napthyl. Preferably $R^1$ is phenyl or halophenyl such as p-chlorophenyl.

Examples of the group Ph are phenyl, halophenyl, lower alkyl phenyl, di(lower alkyl)phenyl or lower alkoxy phenyl as mentioned above in connection with the group $R^1$. Preferably Ph is phenyl or halophenyl such as o, m-p-chloro or bromophenyl.

The group $R^6$ can be hydrogen or a branched or straight chain lower alkyl group (e.g. methyl, ethyl, propyl or butyl). Preferably $R^6$ is hydrogen.

Particularly preferred compounds of general formula (I) are:

[4,4(or 5,5)-dimethyl-2-imidazolinyl ]-α, α- diphenyl methanol,
2-(chlorodiphenylmethyl)-4,4(or 5,5)-dimethyl-2-imidazoline, and α-(m-chlorophenyl)-[4,4 (or 5,5)-dimethyl-2-imidazolinyl]-α-phenylmethanol and the pharmaceutically acceptable salts thereof.

The compounds of general formula (I) may be prepared by a process in which a ketone of general formula (II)

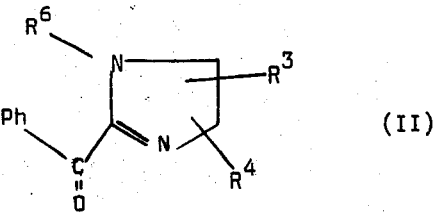

wherein Ph, $R^3$, $R^4$ and $R^6$ have the meanings given above, is reacted with an organometallic compound known in the art for the conversion of a ketone function to the group

and, is desired, a compound in which R represents a hydroxyl groups is converted by a replacement reaction to a compound in which R is halo and , if desired the compound in which R is halo is reacted with a lower alkoxide to give a compound in which R is lower alkoxy or a free base of formula (I) is converted into a pharmaceutically acceptable acid addition salt thereof.

In the above processes the organometallic compound is preferably chosen from (a) Grignard reagents of formula $R^1$MgY wherein Y is halogen and $R^1$ has the meaning defined above, and (b) alkali-metal compounds such as the lithium derivatives of formula $R^1$Li(for example phenyl lithium). The reaction with the organometallic compound is generally carried out in an inert organic solvent, for example ether or tetrahydrofuran, using the standard conditions known for the particular reaction concerned.

As already mentioned, if desired, the compound in which R represents a hydroxyl group may be converted by a replacement reaction into a compound in which R is halo, particularly chloro. For example, the hydroxy compound can be reacted with a hydrohalic acid or an equivalent halogenating agent known for converting alcohols to halides. In a preferred procedure the hydroxy compound is treated with thionyl chloride. The compound in which R is halo, particularly, chloro may be converted into a compound in which R is lower alkoxy by reaction with a lower alkoxide, particularly an alkali metal alkoxide e.g. a sodium alkoxide such as sodium methoxide.

Once a compound of general formula (I) has been prepared any group Ph, R, $R^1$ or $R^6$ may be converted into any other Ph, R, $R^1$ or $R^6$ group by known methods. A hydroxyl function R may be etherified to form a lower alkoxy residue R by the methods described hereinbefore. When $R^6$ is a hydrogen atom the compound can be (lower)alkylated to introduce a lower(alkyl) group $R^6$. If necessary any reactive group in a compound may be protected by known methods before performing any of the above reactions and then removed by known methods subsequent to the reaction.

The starting compounds of general formula (II), may be prepared by oxidation of the corresponding hydroxy compounds of the general formula (III)

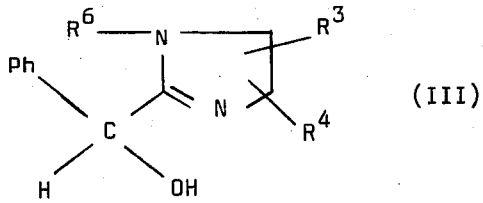

(III)

wherein Ph, $R^3$, $R^4$ and $R^6$ have the meanings given above. Preferably the oxidation is carried out with a mild oxidising agent such as manganese dioxide (for example in a solvent such as dichloromethane, benzene, acetone or aqueous acetone). It may be desirable to use mild oxidising agents such as precipitated manganese dioxide or precipitated manganese dioxide which has been deactivated (e.g. by stirring with water and then drying).

The compounds of general formula (III) are described in the literature or may be prepared by known methods. For example, they may be prepared by the methods described by D.G. Neilson et al., J. Chem. Soc. (C), 1968, 1853, N. W. Bristow, J. Chem. Soc. 1957, 513 or C. H. Tilford et al., J. Amer. Chem. Soc., 1949, 71, 1885.

The compounds of formula (I) are capable of forming acid addition salts with acids, particularly pharmaceutically acceptable acids, and the invention also provides such salts. The salts may be isolated directly from the processes described above or prepared by dissolving the specific compound of formula (I) as its base in a suitable organic solvent, and treating it with a solution of the selected acid, in accordance with conventional procedures for preparing acid addition salts from base compounds generally. As examples of acids, there may be used any of hydrochloric, hydrobromic, tartaric, phosphoric, maleic, citric, acetic or benzoic acid.

The optical isomers of the compounds of formula (I) may be prepared by resolving a racemic mixture by standard methods described in the literature. The racemate may be prepared by any of the processes outlined above. It is to be understood that the resolution may be carried out on the racemic mixture of the final desired product, or it may be carried out on a racemate of one compound of general formula (I) and then the optical isomers subjected to after-processes (such as alkylation or acylation) to give the desired product of formula (I).

The compounds of general formula (I) possess hypoglycaemic activity, as shown by standard tests on warm-blooded animals. The compounds can be tested for hypoglycaemic activity by the following procedure:

Male rats weighing 170-200 grams are fasted overnight. A control blood sample is taken from the tail and the sample of test compound is then administered by stomach tube.

Subsequent blood samples are taken at hourly intervals for 5 hours and the change in the blood sugar concentration is determined. In this procedure it was found that many compounds produced a depression in blood sugar of more than 20% for at least 3 of the hourly test samples when administered at 50 mg/kg or less. Examples of such compounds include: [4,4(or 5,5-dimethyl-2-imidazolinyl]-α, α-diphenylmethanol and 2-(chlorodiphenylmethyl)-4,4(or 5,5)-dimethyl-2-imidazoline.

Many of the compounds possess other pharmacological activity e.g. diuretic, anti-inflammatory and cardiovascular activity. For example many of the compounds show anti-inflammatory properties when tested by the procedures of Winter et al., in Proc. Soc., Biol. Med., 1962, 111, 544 and Buttle et al in Nature, 1957, 179, 629.

Some of the compounds have been tested for diuretic activity by the following procedure: Male rats were fasted for 18 hours (overnight) but had free access to drinking water during this time. Next morning the animal's bladders were emptied by gentle squeezing of the lower abdomen and the compounds were then administered orally as solutions in water. The concentrations of the solutions were adjusted so that each animal received its appropriate dose in a volume equivalent of 25 ml/kg body weight. Pairs of similarly treated animals were placed in metabolism cages (without food or drinking water) and urine was collected for 3 hours. At the end of this period the animal's bladders were emptied as before.

As the compounds of general formula (I) show pharmaceutical activity the invention further provides a pharmaceutical composition which comprises a pharmaceutically active form of a compound provided by the invention in association with a pharmaceutically acceptable carrier. Any suitable carrier known in the art can be used to prepare the pharmacetical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carrier) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound ir orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage can be a capsule or tablet itself, or it can be the appropriate number of any of these in packaged form. The quantity of active ingredient in a unit dose of composition may be varied or adjusted from 5 mg. or less to 500 mg. or more, according to the particular need and the activity of the active ingredient. The invention also includes the compounds in the absence of carrier where the compounds are in unit dosage form.

The following Examples illustrate the invention:

EXAMPLE 1 o-Bromophenyl 4,4(or 5,5)-dimethyl-2-imidazolinyl ketone a. A solution of ethyl o-bromomandelimidate hydrochloride (29.4 g., 0.1 mole) and 1,2-diamino-2-methyl propane (8.8 g., 0.1 mole) in absolute ethanol (150 ml.) was heated under reflux for 5 hours. Removal of the solvent and crystallisation of the residue from isopropanol/ether yielded a crude hydrochloride (23.4g.). An aqueous solution of the crude hydrochloride was basified (NaOH) with simultaneous scratching of the flask to yield α-(o-bromophenyl)-4,4(or 5,5)-dimethyl-2-imidazolinemethanol as the crystalline free base (16.2 g., m.p. 128°-130°). Alternatively the free base may be extracted into chloroform, the extracts dried (MgSO$_4$), and the residue after removal of the solvent triturated with petroleum (60°-80°).

An analytical sample of the hydrochloride was prepared by acidifying a solution of the free base in isopropanol with ethereal HCl, m.p. 213°-217°; [Found: C,45.35; H, 5.05; N, 8.6%; C$_{12}$H$_{15}$BrN$_2$O. HCl requires C, 45.1, H, 5.05; N, 8,75%].

b. A solution of α-(o-bromophenyl)-4,4(or 5,5)-dimethyl-2-imidazolinemethanol (15.8 g.) in dichloromethane (750 ml.) was stirred with precipitated manganese dioxide (150 g.) at room temperature for 40 hours. The manganese dioxide was filtered and stirred with a further portion of dichloromethane (400 ml.) for 1 hour. After filtering the combined filtrates were dried (MgSO$_4$), the solvent removed and the residue recrystallised from petroleum (b.p. 60°-80°) to yield o-bromophenyl 4,4(or 5,5)-dimethyl-2-imidazolinyl ketone (11.01 g., m.p. 107°-108°). [Found: C,51.25; H,4.85; N,10.05%; C$_{12}$H$_{13}$BrN$_2$O requires C, 51.25; H,4.65; N, 9.95%]. o-Chlorophenyl 4,4(or 5,5)-dimethyl-2-imidazolinyl ketone, m.p. 110°-112°C, is prepared in an analogous manner.

EXAMPLE 2 o-Bromophenyl-2-imidazolinyl ketone

A solution of α-(o-bromophenyl)-2-imidazolinemethanol (16.0 g.) in acetone (600 ml.) and water (150 ml.) was stirred with deactivated precipitated manganese dioxide (100 g.) for 24 hours. [The commerical precipitated manganese dioxide was deactivated by stirring with water for 1 hour. and drying in a vacuum oven at ca.65°-70°C for 5 hours]. After filtering and washing the manganese dioxide with acetone, the solution was evaporated to a small volume under reduced pressure, diluted with water and extracted with chloroform. The combined extracts were dried (MgSO$_4$), the solvent removed and the residue allowed to crystallise from a small volume of ether to yield crude o-bromophenyl 2-imidazolinyl ketone (11.5 g.). A sample recrystallised from benzene petroleum (b.p. 60°-80°) had m.p. 149°-151°. [Found: C, 47.9; H, 3.7; N, 11.1%; C$_{10}$H$_9$BrN$_2$O requires C, 47.5; H, 3.6; N, 11.1%].

EXAMPLE 3

2-Imidazolinyl Phenyl ketone.

A suspension of 2-imidazolinyl-phenylmethanol (5.0 g.) in dichloromethane (250 ml.) was stirred at room temperature with deactivated precipitated manganese dioxide (50 g.) for 60 hrs. The product was isolated as in Example 1 and the residue crystallised from benzene/petroleum to yield the title compound as colourless prisms (3.15 g.), m.p. 141°-143°C. [Found C, 68.9; H, 5.8; N, 16.1%—C$_{10}$H$_{10}$N$_2$O— requires C, 68.9; H, 5,8; N, 16.05%].

EXAMPLE 4

α, α-Diphenyl-(2-imidazolinyl)methanol

A solution of 2-imidazolinyl phenyl ketone (3.48 g., ) 0.02 mole) in dry tetrahydrofuran (50 ml.) was added at room temperature to a stirred solution of phenylmagnesium bromide [made from magnesium (1.2 g., 0.05 mole) and bromobenzene (7.9 g. 0.05 mole)] in dry tetrahydrofuran (40 ml.). After addition, the mixture was stirred for 14 hours at room temperature, poured onto ice/ammonium chloride and extracted with chloroform. The combined extracts were washed, dried over magnesium sulphate and the solvent removed. The residue was dissolved in ethanol, acidified with ethereal HCl and the crude hydrochloride allowed to crystallise. A further crystallisation from ethanol/ether after treatment with charcoal yielded the title compound as pure colourless needles (1.71 g.), m.p. dec>215°C, slightly hygroscopic. [Found: C, 64.5; H, 6.2; N, 9.15%; C$_{16}$H$_{16}$N$_2$O.HCl.½H$_2$O requires C, 64.55; H, 6.1; N, 9,35%].

EXAMPLE 5

α-(m-Chlorophenyl)-[4,4(or 5,5)-dimethyl-2-imadazolinyl]-α-phenylmethanol

A solution of 4,4(or 5,5)-dimethyl-2-imidazolinyl phenyl ketone (4.04 g., 0.02 mole) in dry tetrahydrofuran (50 ml.) was added at room temperature to a stirred solution of m-chlorophenylmagnesium bromide [made from magnesium (1.2 g., 0.05 mole) and m-bromochlorobenzene (9.5 g., 0.05 mole)] in dry tetrahydrofurn (40 ml.). The mixture was stirred for 14 hours, poured onto ice/ammonium chloride and extracted with chloroform. The combined extracts were washed, dried over magnesium sulphate, the solvent removed and the residue triturated with petroleum to yield crude white needles. Crystallisation from ethanol-/ethereal HCl yielded the title compound as the pure hydrochloride, m.p. 205°–207°C (dec.). [Found: C, 60.4; H, 5,35; N, 8.15%; $C_{18}H_{19}ClN_2O$. HCl requires C, 60.55; H, 5,8; N, 8.3%].

The following compound was prepared in an analogous manner to the reaction of 4,4(or 5,5)-dimethyl-2-imidazolinyl phenyl ketone with phenylmagnesium bromide: α, α-diphenyl-[4,4(or 5,5)-dimethyl-2-imidazolinyl] methanol hydrochloride, m.p. 210°–213°C.

In a similar manner reaction of 4,4(or 5,5)-dimethyl-2-imidazolinyl phenyl ketone with o-methylphenylmagnesium bromide, 2,6-dimethylphenylmagnesium bromide, 4-methoxyphenylmagnesium bromide and 1-naphthylmagnesium bromide gives, respectively :

α-(o-methylphenyl)-[4,4(or 5,5)-dimethyl-2-imidazolinyl]-α-phenylmethanol,
α-(2,6-dimethylphenyl)-[4,4(or 5,5)-dimethyl-2-imidazolinyl]-α-phenylmethanol,
α-(4-methoxyphenyl)-[4,4(or 5,5)-dimethyl-2-imidazolinyl]-α-phenylmethanol, and
[4,4(or 5,5)-dimethyl-2-imidazolinyl]-α-(1-napthyl)-α-phenylmethanol.

Similarly, reaction of 1,4,4 (or 1,5,5)-trimethyl-2-imidazolinyl phenyl ketone with phenylmagnesium bromide gives 2,2-diphenyl-[1,4,4 (or 1,5,5)-trimethyl-2-imidazolinyl]methanol.

EXAMPLE 6

2-(Chlorodiphenylmethyl)-4,4(or 5,5)-dimethyl-2-imidazoline hydrocholoride

Thionyl chloride (1.1 ml., 0.015 mole) was added dropwise to a stirred solutin of [4,4(or 5,5)-dimethyl-2-imidazoline]diphenylmethanol (1.4 g., 0.005 mole) in dry chloroform. the solution was stirred 1 hour at room temperature and then heated under reflux for 4 hours. On dilution with a little ether the slightly hygroscopic title compound was obtained, (1.6 g., m.p. 196°–200°C). [Found C, 62.7; H, 5.9; N, 8.15%; $C_{18}H_{19}ClN_2·HCl·½H_2O$ requires C, 62,8; H, 6.15; N, 8.15%].

EXAMPLE 7

α-Chlorophenyl 2-imidazolinyl ketone

A solution of o-chlorophenyl-2-imidazolinemethanol (22 g.) in acetone (980 ml.) and water (220 ml.) was stirred for 24 hours at room temperature with manganese dioxide (160 g.) [prepared by treating commercial precipitated manganese dioxide with water and drying in a vacuum oven at 65°–70°C for 5 hrs.]The mixture was filtered, the manganese dioxide washed with acetone and the filtrate concentrated under reduced pressure. After dilution with water, the solution was extracted with chloroform, the combined extracts dried ($MgSO_4$) and the solvent removed. Trituration of the residue with ether yielded the crude ketone (13.9 g.). Crystallisation from benzene after treatment with charcoal yielded an analytical sample, m.p. 128.5°–130°C, [Found: C, 57.9; H, 4,35; N, 13.7% $C_{10}H_9ClN_2O$ requires C, 57.55; H, 4.35; N, 13.4%].

EXAMPLE 8

2-(Methoxydiphenyl)-4,4(or 5,5)dimethyl-2-imidazoline

A solution of 2-(chlorodiphenylmethyl)-4,4(or 5,5) dimethyl-2-imidazoline hydrochloride (0.0025 mole) and sodium methoxide (0.005 mole) in dry methanol (25 ml.) is stirred at room temperature for 2 days. After removal of the solvent the residue is dissolved in chloroform washed with water and dried over magnesium sulphate. Removal of the solvent gives the title compound.

What is claimed is:

1. A compound selected from the group consisting of bases having the formula

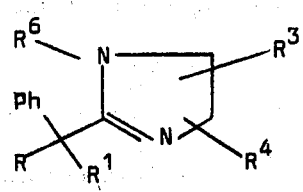

and the pharmaceutically acceptable acid addition salts thereof, wherein $R^3$ and $R^4$ which may be same or different represent a member of the group consisting of hydrogen and lower alkyl, Ph represents a member of the group consisting of phenyl, halophenyl, lower alkyl phenyl, di(lower alkyl)phenyl) and lower alkoxyphenyl, R is a member of the group consisting of hydroxyl, lower alkoxy and chlorine, $R^1$ is a member of the group consisting of phenyl, halophenyl, lower alkyl phenyl, di(loweralkyl)phenyl, lower alkoxy phenyl and naphthyl and $R^6$ is a member of the group consisting of hydrogen and lower alkyl.

2. A compound according to claim 1 which is [4,4(or 5,5)-dimethyl-2-imidazolinyl]-α, α-diphenylmethanol.

3. A compound according to claim 1 which is 2-(chlorodiphenylmethyl)-4,4 (or 5,5)-dimethyl-2-imidazoline.

4. A compound according to claim 1 which is α-(m-chlorophenyl)-[4,4 (or 5,5)-dimethyl-2-imidazolinyl]-α-phenylmethanol.

* * * * *

UNITED STATES PATENT AND TRADEMARK OFFICE
CERTIFICATE OF CORRECTION

PATENT NO. : 3,965,112
DATED : June 22, 1976
INVENTOR(S) : Alan Chapman White and Robin Michael Black It is certified that error appears in the above-identified patent and that said Letters Patent are hereby corrected as shown below:

Title page, item 30, Foreign Priority Data should read:

| December 14, 1971 | United Kingdom | 1250/71 |
| November 30, 1972 | United Kingdom | 11,199/72 |
| March 15, 1972 | United Kingdom | 12,069/72 |

Signed and Sealed this

*Eighteenth* Day of *October 1977*

[SEAL]

*Attest:*

RUTH C. MASON
*Attesting Officer*

LUTRELLE F. PARKER
*Acting Commissioner of Patents and Trademarks*